US00PP18018P2

(12) United States Plant Patent
Dümmen

(10) Patent No.: US PP18,018 P2
(45) Date of Patent: Sep. 11, 2007

(54) ***GERANIUM* PLANT NAMED 'DUEIMPAHOPI'**

(50) Latin Name: *Pelargonium peltatum*
Varietal Denomination: Dueimpahopi

(75) Inventor: Marga Dümmen, Rheinberg (DE)

(73) Assignee: Dümmen Jungpflanzen GbR, Rheinberg, DE (US)

( * ) Notice: Subject to any disclaimer, the term of this patent is extended or adjusted under 35 U.S.C. 154(b) by 0 days.

(21) Appl. No.: 11/349,717

(22) Filed: Feb. 7, 2006

(51) Int. Cl.
*A01H 5/00* (2006.01)

(52) U.S. Cl. ..... Plt./332
(58) Field of Classification Search ..... Plt./332
See application file for complete search history.

(56) References Cited

U.S. PATENT DOCUMENTS

PP15,750 P2 * 5/2005 Dummen ..... Plt./332

OTHER PUBLICATIONS

UPOV ROM GTITM Computer Database, GTI Jouve Retrieval Software 2006/05 Citation for 'Dueimpahopi'.*

* cited by examiner

*Primary Examiner*—Wendy Haas
(74) *Attorney, Agent, or Firm*—C. A. Whealy

(57) ABSTRACT

A new and distinct cultivar of Ivy *Geranium* plant named 'Dueimpahopi', characterized by its upright and outwardly spreading plant habit; vigorous growth habit; freely branching habit; freely flowering habit; and dark pink-colored single flowers.

1 Drawing Sheet

Botanical denomination: *Pelargonium peltatum.*
Cultivar designation: 'Dueimpahopi'.

CROSS-REFERENCE TO RELATED APPLICATIONS

The present application is co-pending with the following related application U.S. Plant patent application Ser. No. 11/349,720: Title: *Geranium* Plant Named 'Duepamerl' Applicant: Marga Dümmen

BACKGROUND OF THE INVENTION

The present invention relates to a new and distinct cultivar of Ivy *Geranium* plant, botanically known as *Pelargonium peltatum,* and hereinafter referred to by the name 'Dueimpahopi'.

The new Ivy *Geranium* is a product of a planned breeding program conducted by the Inventor in Rheinberg, Germany. The objective of the breeding program was to develop new freely-flowering Ivy *Geraniums* with attractive flower and foliage colors.

The new Ivy *Geranium* originated from a cross-pollination made by the Inventor on Jul. 1, 2000, of a proprietary selection of *Pelargonium peltatum* identified as code number F-16-09, not patented, as the female, or seed, parent with a proprietary selection of *Pelargonium peltatum* identified as code number F-23-09, not patented, as the male, or pollen, parent. The cultivar Dueimpahopi was discovered and selected by the Inventor as a flowering plant within the progeny from this cross in a controlled environment in Rheinberg, Germany on Jul. 1, 2004.

Asexual reproduction of the new cultivar by terminal vegetative cuttings at Rheinberg, Germany since Jul. 1, 2004 has shown that the unique features of this new Ivy *Geranium* are stable and reproduced true to type in successive generations of asexual reproduction.

SUMMARY OF THE INVENTION

The following traits have been repeatedly observed and are determined to be the unique characteristics of 'Dueimpahopi'. These characteristics in combination distinguish 'Dueimpahopi' as a new cultivar and distinguish it from other known Ivy *Geranium* cultivars:

1. Upright and outwardly spreading plant habit.
2. Vigorous growth habit.
3. Freely branching habit.
4. Freely flowering habit.
5. Dark pink-colored single flowers.

Plants of the new Ivy *Geranium* can be compared to plants of the parent selections. Plants of the new Ivy *Geranium* are more vigorous than plants of the female parent selection. In addition, plants of the new Ivy *Geranium* and female parent selection differ in flower color as plants of the female parent selection have red purple-colored flowers. Plants of the new Ivy *Geranium* are more vigorous and have larger flowers than plants of the male parent selection.

Plants of the new Ivy *Geranium* differs from plants of the cultivar Duepamerl, disclosed in U.S. Plant patent application Ser. No. 11/349,720, primarily in flower color. In addition, plants of the new Ivy *Geranium* have single flowers whereas plants of the cultivar Duepamerl have double flowers.

The new Ivy *Geranium* can be compared to plants of the cultivar Wico, not patented. In side-by-side comparisons conducted in Rheinberg, Germany, plants of the new Ivy *Geranium* differed from plants of the cultivar Wico in the following characteristics:

1. Plants of the new Ivy *Geranium* were more vigorous than plants of the cultivar Wico.
2. Plants of the new Ivy *Geranium* had larger leaves and larger flowers than plants of the cultivar Wico.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Ivy *Geranium*. The photograph comprises a side perspective view of a typical flowering plant of 'Dueimpahopi' grown in a container.

DETAILED BOTANICAL DESCRIPTION

The cultivar Dueimpahopi has not been observed under all possible environmental conditions. The phenotype may vary somewhat with variations in environment, such as temperature and light intensity, without, however, any variance in genotype.

The aforementioned photograph, following observations and measurements describe plants grown in Rheinberg, Germany during the summer under commercial practice in a glass-covered greenhouse with day and night temperatures about 18° C. and light levels about 4,500 foot-candles. Plants were grown in 10.5 cm containers. Plants were pinched about three weeks after planting. Plants were about eight weeks from planting when the photograph and the detailed botanical description were taken. In the following description, color references are made to The Royal Horticultural Society Colour Chart, 1995 edition, except where general terms of ordinary dictionary significance are used.

Botanical classification: *Pelargonium peltatum* cultivar Dueimpahopi.

Parentage:

*Female parent.*—Proprietary selection of *Pelargonium peltatum* identified as code number F-16-09, not patented.

*Male parent.*—Proprietary selection of *Pelargonium peltatum* identified as code number F-23-09, not patented.

Propagation:

*Type cutting.*—Terminal vegetative cuttings.

*Time to initiate roots.*—Summer: About 5 days at 20° C. Winter: About 7 days at 20° C.

*Time to develop roots.*—Summer: About three weeks at 20° C. Winter: About four weeks at 20° C.

*Root description.*—Fine; fibrous; white in color.

*Rooting habit.*—Freely branching.

Plant description:

*General appearance.*—Upright and outwardly spreading plant habit, rounded plant form; densely foliated.

*Growth and branching habit.*—Moderately vigorous. Freely branching, about four lateral branches per plant.

*Plant height.*—About 20 cm.

*Plant width.*—About 12 cm.

*Lateral branches.*—Length: About 18 cm. Internode length: About 4.5 cm. Texture: Smooth. Color: 144A.

*Foliage description.*—Arrangement: Alternate, single. Length: About 6.9 cm. Width: About 8.3 cm. Shape: Reniform. Apex: Acute. Base: Peltate. Margin: Crenate. Venation pattern: Palmate. Texture, upper and lower surfaces: Smooth, glabrous. Color: Developing and fully expanded foliage, upper surface: 137B; zonation pattern, 137A in color and about 1.5 cm in width; venation, 144A. Developing and fully expanded foliage, lower surface: 144A; venation, 144A. Petiole: Length: About 6 cm. Diameter: About 2.2 cm. Color, upper and lower surfaces: 144A.

Flower description:

*Flower arrangement.*—Dark pink-colored single flowers arranged in rounded hemispherical umbels arising from apical leaf axils. Umbels displayed above the foliage on peduncles. Flowers rounded in form. Umbels persistent, flowers not persistent. Flowers not fragrant.

*Quantity of flowers.*—Freely flowering; plants have about four to six opening and fully open umbels each with about nine to twelve flowers per umbel.

*Flowering season.*—Flowering continuous spring through summer.

*Flower longevity.*—Flowers last about five to seven days on the plant.

*Umbel size.*—Diameter: About 10.8 cm. Height: About 5.5 cm.

*Flower size.*—Diameter: About 4.9 cm. Depth (height): About 2.3 cm.

*Flower buds.*—Length: About 1.4 cm. Diameter: About 7 mm. Shape: Ovoid. Color: 144A.

*Petals.*—Quantity per flower: Five. Length: About 3 cm. Width: About 2 cm. Shape: Obovate. Apex: Rounded. Base: Attenuate. Margin: Sinuate. Texture, upper and lower surfaces: Smooth. Color: When opening and fully opened, upper surface: 67D; towards the base, 53B; color becoming closer to 62A with development. When opening and fully opened, lower surface: 62A; towards the base, 53B.

*Sepals.*—Quantity per flower: About five to six arranged in a single whorl. Length: About 1.4 cm. Width: About 4 mm. Shape: Elongated, tapering. Apex: Apiculate. Margin: Entire. Texture, upper and lower surfaces: Smooth, glabrous. Color, upper and lower surfaces: 144A.

*Peduncle* (*umbel stem*).—Length: About 13 cm. Diameter: About 1 cm. Angle: Erect. Strength: Moderately strong. Texture: Smooth, glabrous. Color: 144A.

*Pedicel* (*individual flower stem*).—Length: About 2.7 cm. Diameter: About 2 mm. Angle: Erect. Strength: Moderately strong. Texture: Pubescent. Color: 144A overlain with 178A.

*Reproductive organs.*—Androecium: Anther quantity per flower: About nine. Anther length: About 3 mm. Anther shape: Ovate. Anther color: 60A. Pollen amount: Moderate. Pollen color: 28A. Gynoecium: Pistil quantity per flower: One. Pistil length: About 1.1 cm. Stigma shape: Crested. Stigma color: 60A to 60B. Style length: About 4 mm. Style color: 2D. Ovary color: Close to 144A.

*Seed/fruit.*—Development of seeds and fruit have not been observed.

Disease/pest resistance: Plants of the new Ivy *Geranium* have not been observed to be resistant to pathogens and pests common to Ivy *Geraniums*.

Temperature tolerance: Plants of the new Ivy *Geranium* have been observed to be tolerant to temperatures ranging from about 5° C. to about 40° C.

It is claimed:

1. A new and distinct cultivar of Ivy *Geranium* plant named 'Dueimpahopi', as herein illustrated and described.

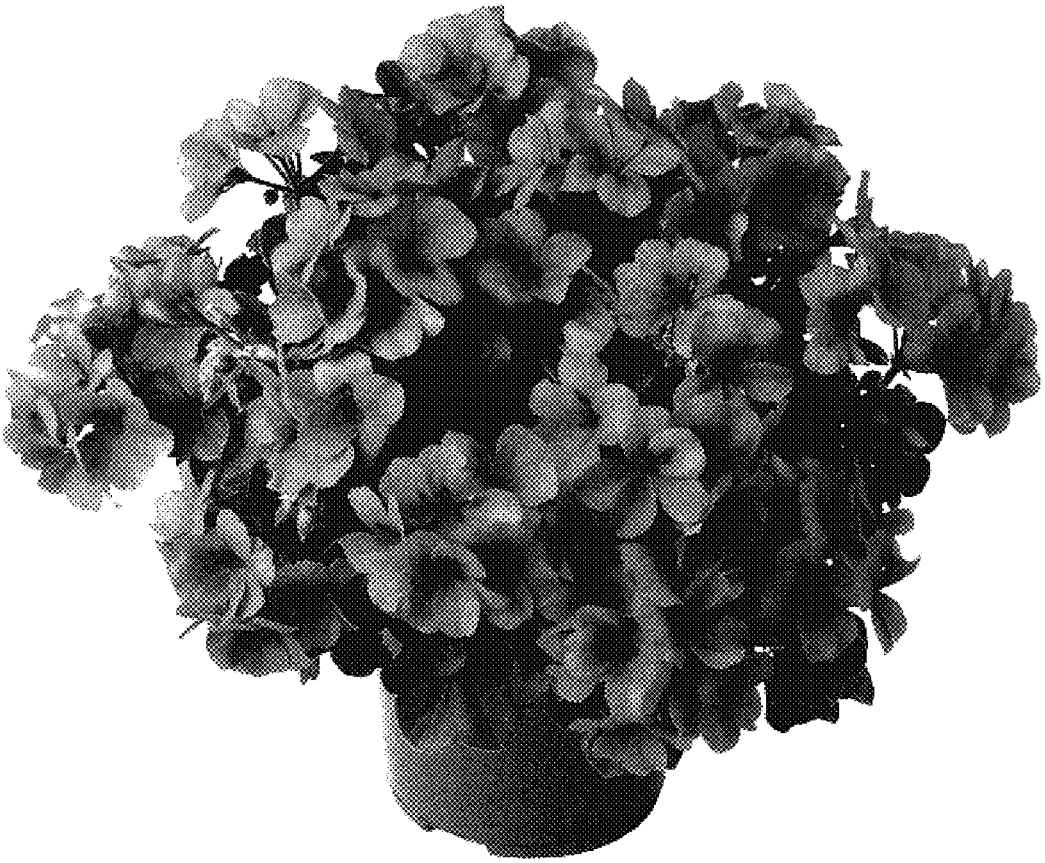

* * * * *